United States Patent [19]
Roberts et al.

[11] Patent Number: 5,603,698
[45] Date of Patent: Feb. 18, 1997

[54] PROSTHESIS DELIVERY SYSTEM

[75] Inventors: George T. Roberts, Weston; Darin Wilson, Wellesley, both of Mass.; Erik Andersen, Jyllinge, Denmark; Hans-Peter Strohband, Erkrath, Germany

[73] Assignee: Boston Scientific Corporation, Watertown, Mass.

[21] Appl. No.: 538,175

[22] Filed: Aug. 23, 1995

Related U.S. Application Data

[63] Continuation of Ser. No. 46,237, Apr. 13, 1993, abandoned.

[51] Int. Cl.$^6$ ................................................. A61M 29/00
[52] U.S. Cl. .......................... 604/104; 606/108; 606/191; 606/198; 623/12
[58] Field of Search ................................. 606/151, 199, 606/108, 191, 194, 198, 195–197, 200; 623/1, 12, 11; 604/265.8, 93, 96, 281, 104, 280

[56] References Cited

U.S. PATENT DOCUMENTS

| | | |
|---|---|---|
| 1,878,671 | 9/1932 | Cantor . |
| 2,701,559 | 2/1955 | Cooper . |
| 3,334,629 | 8/1967 | Cohn . |
| 3,540,431 | 11/1970 | Mobin-Uddin . |
| 3,638,649 | 2/1972 | Ersek . |
| 3,657,744 | 4/1972 | Ersek . |
| 3,736,939 | 6/1973 | Taylor . |
| 3,774,596 | 11/1973 | Cook . |
| 3,811,423 | 5/1974 | Dickinson, III et al. . |
| 3,868,956 | 3/1975 | Alfidi et al. . |
| 3,889,685 | 6/1975 | Miller, Jr. et al. . |
| 3,938,529 | 2/1976 | Gibbons . |

(List continued on next page.)

FOREIGN PATENT DOCUMENTS

| | | |
|---|---|---|
| 0183372 | 6/1986 | European Pat. Off. . |
| 0364787 | 4/1990 | European Pat. Off. . |
| 0461791 | 12/1991 | European Pat. Off. . |
| 0508473 | 11/1992 | European Pat. Off. . |
| 83/00997 | 3/1983 | WIPO . |
| 83/03752 | 11/1983 | WIPO . |
| 87/04935 | 8/1987 | WIPO . |
| 93/17636 | 9/1993 | WIPO . |
| 94/12136 | 6/1994 | WIPO . |
| 94/24961 | 11/1994 | WIPO . |

OTHER PUBLICATIONS

Schneider, Pfizer, Wallstent® Literature, 1994.
Schneider, Pfizer, Wallstent® Literature, 1993.
Kynrim et al., "A Controlled Trial of an Expansile Metal Stent for Pilliation of Esophageal Obstruction Due to Inoperable Cancer" *The New England Journal of Medicine*, vol. 329, No. 18, pp. 1302–1306, Oct. 1993.
Schneider, Pfizer, Wallstent® Literature, 1992.
Schneider, Pfizer, Wallstent® Literature, 1992, Wallstent® Endoprosthesis Endoscopic Stent Placement, for Treatment of Biliary Strictures.
Schneider, Pfizer, Wallstent® Literature, 1991.

(List continued on next page.)

*Primary Examiner*—Corrine M. McDermott
*Assistant Examiner*—Ronald K. Stright, Jr.
*Attorney, Agent, or Firm*—Fish & Richardson P.C.

[57] ABSTRACT

This invention provides prosthesis delivery systems with atraumatic tips that can be dislodged from the catheter so that the catheter can be easily removed from the body after expanding the prosthesis, by pulling the catheter proximally. With the tip dislodged, the catheter, which is of smaller diameter than the tip can be removed even in instances where the prosthesis does not expand the lumen to a large diameter. This invention also provides prosthesis delivery systems with a contoured protective outer sheath having smaller diameters in proximal portions that normally are acutely bent when the system is in the body, than in distal portions corresponding to the position of the prostheses. These systems are more flexible and the sheaths less likely to kink, especially when configured as part of a large delivery system.

21 Claims, 10 Drawing Sheets

U.S. PATENT DOCUMENTS

| | | |
|---|---|---|
| 4,140,126 | 2/1979 | Choudhury . |
| 4,315,509 | 2/1982 | Smit . |
| 4,501,264 | 2/1985 | Rockey . |
| 4,503,569 | 3/1985 | Dotter . |
| 4,512,338 | 4/1985 | Balko et al. . |
| 4,531,933 | 7/1985 | Norton et al. . |
| 4,553,545 | 11/1985 | Maass et al. . |
| 4,580,568 | 4/1986 | Gianturco . |
| 4,603,152 | 7/1986 | Laurin et al. ............................ 604/265 |
| 4,610,657 | 9/1986 | Densow . |
| 4,649,922 | 3/1987 | Wiktor . |
| 4,655,771 | 4/1987 | Wallstén . |
| 4,665,918 | 5/1987 | Garza et al. ............................ 606/108 |
| 4,681,110 | 7/1987 | Wiktor . |
| 4,732,152 | 3/1988 | Wallsten et al. . |
| 4,739,762 | 4/1988 | Palmaz . |
| 4,762,128 | 8/1988 | Rosenbluth . |
| 4,768,507 | 9/1988 | Fischell et al. . |
| 4,776,337 | 10/1988 | Palmaz . |
| 4,793,348 | 12/1988 | Palmaz . |
| 4,878,906 | 11/1989 | Lindemann et al. . |
| 4,886,062 | 12/1989 | Wiktor . |
| 4,893,623 | 1/1990 | Rosenbluth . |
| 4,922,905 | 5/1990 | Strecker . |
| 4,950,227 | 8/1990 | Savin et al. . |
| 5,026,377 | 6/1991 | Burton et al. . |
| 5,049,138 | 9/1991 | Chevalier et al. ..................... 604/265 |
| 5,078,720 | 1/1992 | Burton et al. .......................... 606/108 |
| 5,078,725 | 1/1992 | Enderle et al. . |
| 5,158,548 | 10/1992 | Lau et al. . |
| 5,180,366 | 1/1993 | Woods . |
| 5,180,368 | 1/1993 | Garrison . |
| 5,192,289 | 3/1993 | Jessen . |
| 5,195,984 | 3/1993 | Schatz . |
| 5,234,457 | 8/1993 | Andersen . |
| 5,344,425 | 9/1994 | Sawyer . |
| 5,360,401 | 11/1994 | Turnland . |
| 5,373,854 | 12/1994 | Kolozsi . |
| 5,387,235 | 2/1995 | Chuter . |
| 5,405,380 | 4/1995 | Gianotti et al. . |

OTHER PUBLICATIONS

Adam et al., "Self–Expandable Stainless Steel Endoprostheses for Treatment of Malignant Bile Duct Obstruction" *American Journal of Roentgenology*, vol. 156, Feb. 1991.

Hackethorn et al., "Antegrade Internal Ureteral Stenting" A Technical Refinement, *Radiology*, 156:827–828, Jul., 1985.

Becker et al., "Placement of Double–Pigtail Ureteral Stent Via Cystoscope," *Urology*, XX:310–311, Sep. 1982.

Leadbetter, "Diagnostic Urologic Instrumentation," pp. 358–374 (date unknown).

Microvasive, "Ultraflex Esophageal Prosthesis," Brochure May 1992.

Zollikofer et al., "Endovascular Stenting of Veins and Grafts: Preliminary Clinical Experience", *Interventional Radiology*, Jun. 1988, pp. 707–712.

Sigwart et al., "Intravascular Stents to Prevent Occlusion and Restenosis After Transluminal Angioplasty", *The New England Journal of Medicine*, Mar. 19, 1987, vol. 316, No. 12, pp. 701–706.

Schaer et al., "Treatment of malignant esophageal obstruction with silicone–coated metallic self–expanding stents", *Gastrointestinal Endoscopy*, 1992, vol. 38, No. 1, pp. 7–11.

Rosseau et al., "Self–expanding Endovascular Prosthesis: An Experimental Study", *Radiology*, Sep. 1987, vol. 164, No. 3, pp. 709–714.

Roubin et al., "Early and late results of intracoronary arterial stenting after coronary angioplasty in dogs", *Laboratory Investigation–Coronary Artery Disease*, Oct. 1987, vol. 76, No. 4, pp. 891–897.

Rösch et al., "Experimental Intrahepatic Portacaval Anastomosis: Use of Expandable Gianturco Stents", *Radiology*, Feb. 1987, vol. 162, No. 2, pp. 481–485.

Palmaz et al., "Expandable Intraluminal Graft: A Preliminary Study", *Radiology*, Jul. 1985, vol. 156, No. 1, pp. 73–77.

Palmaz et al., "Atherosclerotic Rabbit Aortas: Expandable Intraluminal Grafting", *Radiology*, Sep. 1986, vol. 160, No. 3, pp. 723–726.

Mills et al., "Avoidance of Esophageal Stricture Following Severe Caustic Burns by the Use of an Intraluminal Stent", *The Annals of Thoracic Surgery*, Jul. 1979, vol. 28, No. 1, pp. 60–65.

Microvasive®, Boston Scientific Corporation, Strecker™ Stent patent literature, 1990.

Medi–tech®, Boston Scientific Corporation, Strecker™ Stent product literature, 1990.

Medi–tech®, Boston Scientific Corporation, Strecker™ Stent product literature, 1991.

Matsumoto et al., "Tantalum Vascular Stents: In Vivo Evaluation with MR Imaging", *Radiology*, 1989, vol. 170, No. 3, pp. 753–755.

Loizou et al., "Treatment of malignant strictures of the cervical esophagus by endoscopic intubation using modified endoprostheses", *Gastrointestinal Endoscopy*, 1992, vol. 38, No. 2, pp. 158–164.

Lawrence Jr. et al., "Percutaneous Endovascular Graft: Experimental Evaluation", *Cardiovascular Radiology*, May 1987, vol. 163, No. 2, pp. 357–360.

Duprat et al., "Flexible Balloon–expanded Stent for Small Vessels", *Radiology*, Jan. 1987, vol. 162, No. 1, pp. 276–278.

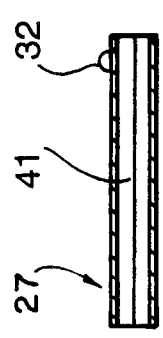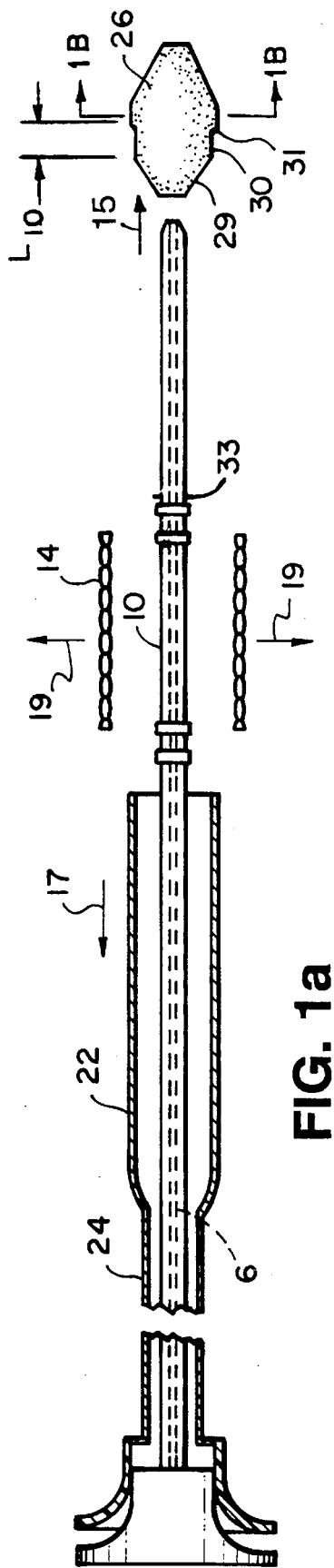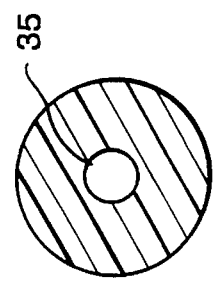
FIG. 1c
FIG. 1a
FIG. 1b

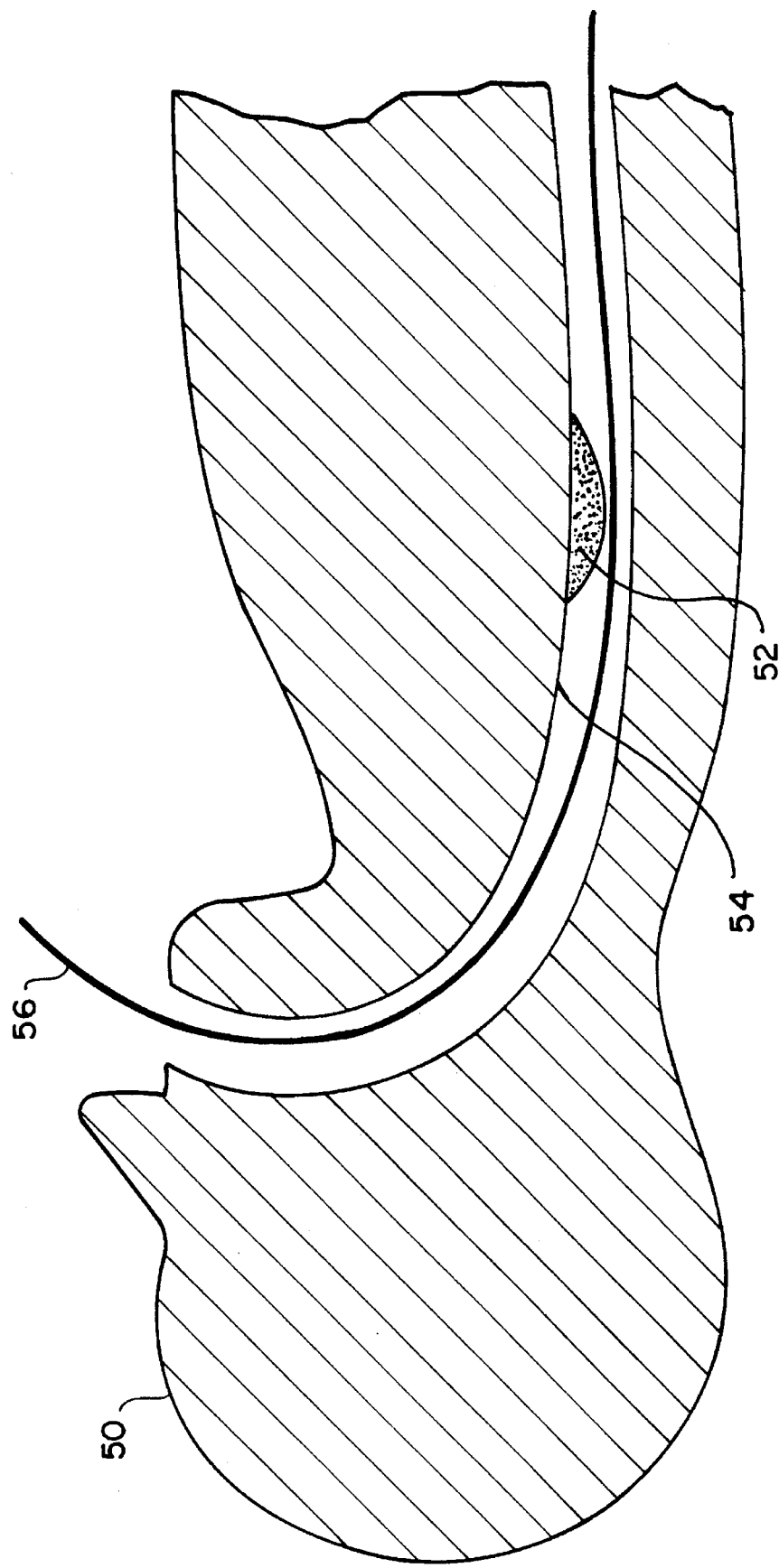

PROSTHESIS DELIVERY SYSTEM

This is a continuation of application Ser. No. 08/046,237 filed Apr. 13, 1993, now abandoned.

FIELD OF THE INVENTION

This invention relates to systems for delivering prostheses into the body.

BACKGROUND OF THE INVENTION

Prostheses, such as stents, grafts, and the like, are placed within the body to improve the function of a body lumen. For example, stents with substantial elasticity can be used to exert a radial force on a constricted portion of a lumen wall to open the lumen to near normal size.

These stents can be delivered into the lumen using a system which includes a catheter, with the stent supported near its distal end, and a sheath, positioned coaxially about the catheter and over the stent, to prevent abrasion between the stent and body wall as the catheter is directed through torturous body pathways. The catheter may have an enlarged tip adjacent the distal end of the stent that also helps to atraumatically advance the system and protects the stent.

Once the stent is located at the constricted portion of the lumen, the sheath is removed to expose the stent, which is expanded so it contacts the lumen wall, The catheter is subsequently removed from the body by pulling it in the proximal direction, through the larger lumen diameter created by the expanded prosthesis, which is left in the body.

SUMMARY OF THE INVENTION

This invention provides prosthesis delivery systems with atraumatic tips that can be dislodged from the catheter so that the catheter can be easily removed from the body after expanding the prosthesis, by pulling the catheter proximally. With the tip dislodged, the catheter, which is of smaller diameter than the tip, can be removed even in instances where the prosthesis does not immediately expand the lumen to provide clearance for the tip. This invention also provides prosthesis delivery systems with a contoured protective outer sheath having smaller diameters in proximal portions that normally are acutely bent when the system is in the body, than in distal portions that correspond to the position of the prosthesis. These sheaths improve flexibility of the system and are less likely to kink, especially when configured as part of a large delivery system. The features of the following aspects can be combined in various ways.

In one aspect, the invention features a system for delivering a prosthesis into the body of a patient. The system has an elongated catheter with a proximal end that remains outside the body, a distal end, and a supporting portion supporting a prosthesis in a radially compacted form for delivery of the prosthesis to a desired location inside the body. The system also includes a dislodgeable atraumatic entry tip distal of the prosthesis. The tip has a diameter about equal to or greater than the radially compacted prosthesis and is selectively dislodgeable from the catheter when the catheter is in the body.

Various aspects may also include one or more of the following features. The tip is friction fit on the catheter and can be removed by providing relative motion between the catheter and the tip with an axial force sufficient to slide the tip off the distal end of the catheter. The prosthesis is expandable to diameters less than the diameter of the tip and the axial force is provided by engaging the prosthesis and the tip by withdrawing the catheter proximally. The friction fit is overcome by an axial force of about 4 lbs. or less. The tip is formed of a material which dissolves upon exposure to body fluids. The tip is formed of a substantially non-body fluid soluble polymer and is shaped and sized to pass the body. The tip has a generally cylindrical shape with a maximum diameter of about 8 mm. The prosthesis is self-expanding. The prosthesis is held in a radially compacted form by a material which dissolves upon exposure to body fluids to thereby expand the stent. The system has a protective sheath over the stent, that engages the tip to form a seal that protects the prosthesis from exposure to body fluids prior to removal of the sheath to expose the prosthesis. The tip is formed of a material that dissolves upon exposure to body fluids more slowly than the material that holds the stent in radially compacted form. The system includes a protective sheath, coaxially disposed about the prosthesis, where the sheath is retractable in the proximal direction to expose the prosthesis to the body of a patient and extendable in the distal direction to engage the tip to slide the tip from the distal end of the catheter. The tip includes a step portion for engaging the sheath without substantial increase in diameter. The sheath has a diameter larger than the radially compacted prosthesis over a length sufficient to extend the sheath distally without engaging the prosthesis and a smaller diameter in proximal portions. The catheter has a highly flexible distal end, extending beyond the tip, and the tip tapers to the diameter of the flexible end.

In another aspect, the invention features a system for delivering a large prosthesis into a large, torturous body lumen of a patient. The system includes an elongated catheter having a proximal end that remains outside the body, a distal end, and a supporting portion proximal of the distal end supporting a prosthesis. The prosthesis has a radially compacted form for delivery of the prosthesis at a desired location inside the body. The system also includes a thin-walled protective sheath having a distal portion with a diameter of about 6 mm or more, coaxially disposed about the large prosthesis during delivery into the body, and a proximal portion with a smaller diameter coaxially disposed about a substantial length of the catheter normally positioned along a torturous path in the body when the device is in use. The sheath is retractable to expose the prosthesis.

Various aspects may also include one or more of the following features. The sheath is formed of a flexible polymer. The prosthesis is a self-expanding prosthesis held in a compacted radial form by means other than the sheath. The proximal portion is substantially the entire length of the sheath proximal of the distal portion. The gap between the proximal portion of the sheath and corresponding portions of the catheter is no greater than about 2.0 mm. The gap between the distal portion of the sheath and the prosthesis is no greater than about 1 mm.

In another aspect, the invention features a method for delivering a prosthesis into the body of a patient. The method includes providing an elongated catheter having a proximal end that remains outside the body, a distal end, and a supporting portion supporting a prosthesis in a radially compacted form. The catheter further includes an atraumatic removable tip distal of the prosthesis with a diameter about equal to or greater than the radially compacted prosthesis. The method includes placing the catheter into a body lumen and positioning the prosthesis at a desired location, expanding the prosthesis to a diameter no larger than the diameter of the tip, removing the tip from the catheter, and withdrawing the catheter through the expanded prosthesis.

Various aspects may also include one or more of the following features. Removing the tip may include withdrawing the catheter so that the tip engages the prosthesis, and continuing to withdraw the catheter so the tip slides axially off the end of the prosthesis. The method may include selecting a self-expanding prosthesis to provide axial force to the interior of the lumen to fully expand the lumen after an extended period of time, and withdrawing the catheter prior to fully expanding the prosthesis. The method may include providing a catheter with a thin-walled protective sheath having a distal portion with a diameter of about 8 mm or more, coaxially disposed about the large prosthesis during delivery into the body, and the sheath further including a proximal portion with a smaller diameter coaxially disposed about a substantial length of the catheter normally positioned along a torturous path in the body when the device is in use, and retracting the sheath to expose the prosthesis. The body lumen may be the esophagus.

The inventions have many advantages. For example, since the catheter can be easily removed from the body when the atraumatic tip has been disengaged, the physician does not have to wait until the prosthesis expands to a radial dimension larger than the tip or use a separate dilatation catheter to expand the lumen so that the catheter can be removed. With systems according to the invention, the physician can even select a prosthesis that will produce a predetermined slow expansion of the lumen, over a period of hours or even days, which can have therapeutic benefits such as avoiding rupture of a lumen wall that has been weakened by a tumor. The catheter can be removed from the body immediately after release of the slow-expanding prosthesis since the small diameter catheter can pass through an even slightly expanded prosthesis, once the atraumatic tip is disengaged. The operability of delivery systems is also improved by using a protective sheath with a smaller diameter in portions proximal of the prosthesis. The flexibility of the delivery system is increased and the sheath kinking is decreased, especially in proximal portions which are likely to be positioned in a torturous portion of a body lumen when the device is in use.

Further features and advantages follow.

BRIEF DESCRIPTION OF THE DRAWINGS

We first briefly describe the drawings.

FIG. 1 is a cross-sectional side view of a system according to the invention configured for delivery into the body, while FIG. 1a is a similar view of the system in an alternate configuration, FIG. 1b is an end-on cross-sectional view of the automatic tip taken along the lines 1b in FIG. 1a; and FIG. 1c is a cross-sectional view of a safety sleeve of the system;

DESCRIPTION OF THE PREFERRED EMBODIMENTS

Structure

Figure 1:
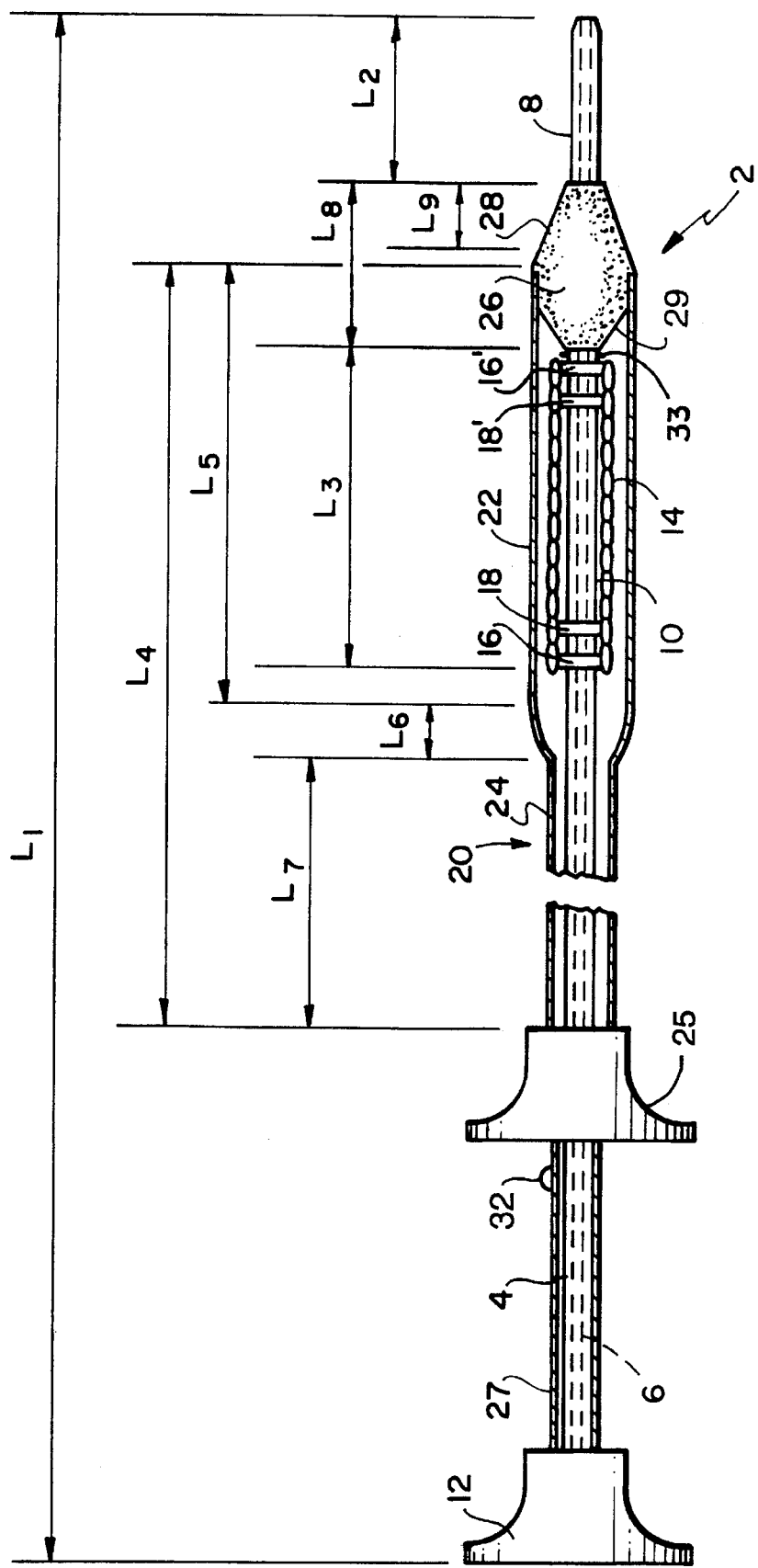

Referring to FIGS. 1 and 1a, a delivery system 2 according to the invention for operation in the esophagus includes a catheter 4 with a stent 14 positioned near the distal end.

The system also includes sheath 20, with a reduced diameter portion 24 proximal of a portion 22 for covering the stent 14 during entry into the body (FIG. 1). The sheath 20 can be retracted (arrow 17) to expose and expand (arrow 19) the stent (FIG. 1a). An atraumatic tip 26, can be disengaged (arrow 15) from the end of the catheter (FIG. 1a).

The catheter 4 has an overall length, $L_1$, about 100 cm, with a constant outer diameter of about 3.4 mm. The catheter 4 (PEBAX, a polyether, polyamid mix forming a block polymer, 70 durometer, Atochem, Philadelphia, Pa.) includes a handle 12 (nylon) on the proximal end, an inner lumen 6 (phantom), of about 1.1 mm inner diameter, for tracking over a guidewire (e.g., 0.038 inch). The catheter 4 may include a stainless steel hypotube (not shown) along the wall of its internal lumen and a permanently attached flexible distal end 8, of length, $L_2$, about 3 cm, formed of a soft polymer (PEBAX, 40 durometer, Atochem) that flexes easily when challenged by a lumen wall, for atraumatic advance.

The catheter 4 includes a supporting portion 10, of length $L_3$, about 15 cm, for supporting the stent 14 in a radially compacted form during delivery into the body. The stent 14 is preferably a self-expanding knitted stent formed of a highly elastic material such as a nitinol-type material (Strecker Stent, Boston Scientific, Watertown, Mass.). Knitted stents are discussed in detail in Strecker, U.S. Pat. No. 4,922,905 and U.S. patent application Ser. No. 07/960,584, filed Oct. 13, 1992, now abandoned, the entire contents of these cases being hereby incorporated by reference. The stent has a maximum expanded diameter of about 20 mm. As mentioned, a stent may be selected to apply a constant, rather gentle radial force to the lumen wall that expands the wall to near normal diameter over an extended period, for example, 24 or 48 hours. The stent is radially compacted by wrapping it about the portion 10 and fixing it in this form using a body-fluid degradable gelatin material. The stent in the compacted form has an outer diameter of about 6.5 mm. Compacting the stent by wrapping it onto a catheter and holding it with gelatin is discussed in U.S. application Ser. No. 07/773,847, filed Oct. 9, 1991, now U.S. Pat. No. 5,234,457, the entire contents of which is also hereby incorporated by reference.

The supporting portion 10 includes radiopaque markers 16, 16' which mark the location of the proximal and distal ends of the stent in the compacted form. The portion 10 also includes radiopaque markers 18, 18' which indicate the ends of the stent 14 in the expanded state.

Positioned coaxially about the catheter 4, and extending over the stent 14 during delivery into the body (FIG. 1), is protective sheath 20. The sheath 20 has an overall length $L_4$, about 70 cm, is formed of a single piece of extruded flexible polymer (extruded PEBAX, 70 durometer, available from Atochem) and has a constant wall thickness of about 0.5 mm. The sheath includes a distal portion 22 having a length, $L_5$, about 17 cm, which corresponds approximately to the length of the stent in compacted form with some extension on either end. The outer diameter of the distal portion 22 of the sheath is about 8 mm and the inner diameter is slightly larger than the diameter of the stent 14 in its compacted form, to provide a clearance of about 0.5 mm between the inner wall of the sheath and the compacted stent. The sheath 20 further includes a tapered portion of length, $L_6$, about 7–9 cm, from the larger diameter of the distal portion 22 to the smaller diameter, about 5 mm, of a proximal portion 24 which has a length, $L_7$, about 53 cm. A handle 25 (nylon) allows the sheath to be retracted from the proximal end (arrow 17) to expose the stent so that it can be expanded (arrows 19). (The distance between the handle 25 on the sheath, and handle 12, on the catheter, corresponds approximately to the length of the compacted stent.) A safety sleeve 27 with a slit 41 and pull tab 32 is positioned between the handles during delivery to prevent inadvertent exposure of the stent (FIG. 1). The sleeve 27 is stripped from the catheter once the system is properly placed so the sheath can be retracted to expose the stent (FIG. 1*a*). The diameter of the proximal portion 24 is selected to conform closely to the outer diameter of the catheter body 4. The clearance between the outer diameter of the catheter body 4 and the inner diameter of the proximal portion 24 of the sheath 20 is about 1.5 mm.

The sheath, having variable radial dimension along its length, is a particular feature of the invention which enhances positioning of a large stent with large delivery systems for use in lumens having torturous pathways. Since the outer diameter of the proximal portion of the sheath is small, the flexibility is enhanced. It flexes more easily around torturous channels because there is less strain on the outside curved wall and less compaction on the inside curved wall. Since all portions of the sheath conform more closely to the outer diameter of the components within the sheath, kinking along the length is reduced. The gap between the outer diameter of the catheter and inner diameter of the sheath is small, so the catheter tends to support the relatively thin-walled sheath when the system is bent around a curve. In the distal portion of the sheath, the larger radial dimension is supported by the larger radial dimension of the stent, which is positioned around the catheter. Minimizing kinking is an important feature, since severe kinking can cause friction between the sheath and the catheter that can prevent the sheath from being retracted. In many body lumens, such as the esophagus, the most torturous portion of the lumen is near the point of entry of the body. The present system improves operation by enhancing flexibility and reducing kinking particularly in the proximal portions of the device typically located along a torturous bend. The sheath of the system described does not kink in the proximal portions when bent 90 degrees over a radius of about 6.35 cm, which is typical of the esophagus. Moreover, a sheath with reduced size in proximal portions presents a smaller inner surface area, which reduces friction against the catheter, and therefore makes operation smoother.

The system further includes an atraumatic tip 26, with a length, $L_8$, about 0.75 inch, and a maximum outer diameter of about 8 mm. The maximum outer diameter of the tip 26 substantially corresponds to the maximum outer diameter of the distal portion 22 of the sheath. The tip 26 includes a distal taper portion 28 of length, $L_9$, about 0.25 inch, to present a gradual increase in diameter for atraumatic advance. The tip 26 also includes a proximal taper 29 that aids atraumatic engagement of the tip with constricted portions of the lumen when removing the catheter during withdrawal. The distal portion of the sheath meets the tip 26 along a step portion 30 of length, $L_{10}$, about 1 cm. The step portion 30 also includes a slight taper 31 to avoid any sharp edges. The step portion 30 of the tip 26 and the sheath 20 form a seal that isolates the stent from body fluids during delivery into the body to avoid dissolving the gelatin prior to withdrawal of the sheath, which could cause premature expansion of the stent.

The tip 26 is a molded piece with an inner lumen 35 (FIG. 1*b*) of diameter of about 3.4 mm, that substantially corresponds, within a tolerance of about plus or minus 0.03 mm, to the outer diameter of the distal end of the catheter body 4 so the tip can be friction-fit onto the catheter. The tip can be slid off the end of the catheter (arrow 15), which feature is especially important in instances where the stent 14 does not expand to a diameter larger than the outer diameter of the tip. By disengaging the tip 26 from the end of the catheter 4, the catheter and protective sheath can be easily removed from the body, leaving the stent within the body lumen. In this particular embodiment, the tip is meant to be slid off the catheter by withdrawing the catheter so that the tip engages a part of the stent that has expanded to diameters smaller than the tip diameter. The tip is fit so low force, e.g. about 4 lbs., preferably 2 lbs. or less is needed to slide it off the catheter so that the stent is not disturbed during withdrawal of the catheter and removal of the tip. More generally, the stent and fit of the tip are selected so the force needed to slide the tip off is less than force needed to move the stent axially in the body lumen. The sheath 20, contacting the tip in the step portion 30, as discussed above, inhibits axial proximal motion of the tip as the system is urged forward into the lumen during delivery. In addition, the catheter may also include a stop 33, proximal of the tip 26 which also inhibits axial proximal motion. The stop 33 may be formed by crimping the catheter to extend the catheter radially on opposing sides. The stop 33 also prevents the tip from being slid proximally when the sheath is withdrawn to expose the stent. The tip can also be actively slipped off the end of the catheter using, for example, a sheath which can be moved axially distally against the tip, as will be discussed further below. In such cases, the force needed to remove the tip is not dependent on concerns about disturbing the stent.

The tip 26 may be formed of a body fluid soluble polymer, such as polyvinyl alcohol (Vilmex 2019, Air Products, Inc.). The solubility of the polymer forming the tip is selected so that substantial dissolution does not occur during delivery, to avoid prematurely exposing the stent to body fluids. The body fluid soluble polymer of the tip expands somewhat upon initial exposure to body fluids which helps form the seal with the sheath. In the preferred embodiment, the gelatin encasing the stent (DFG STOESS, Duetch Gelatin Fabriken AG, Germany) dissolves in a short time, within about 2 to 8 minutes. The polymer forming the tip 26 does not substantially dissolve over a period of 30 minutes but completely dissolves over a period of about 4 hours or less. Dissolvable polymers are also discussed in U.S. Pat. No. 5,049,138 which is also hereby incorporated by reference.

Alternatively, the tip 26 can be formed of a nondissolvable polymer (Nylon, Vestamid, Hulls, Germany), in which case the shape and size of the tip are kept to allow the tip to pass the body. The tip should have a shape without blunt surfaces and sharp edges, such as a generally cylindrical form as illustrated above, so the tip moves smoothly through the body. In the case of an esophageal stent, the tip remaining in the body should have a maximum diameter of about 8 mm or less. In these embodiments a compressible silicon O-ring, about 1 mm wide, is typically fitted onto the step portion 30 to provide a secure seal against body fluids.

Use

The following procedure may be used for treating a patient with a tumor in the esophagus. The patient is prepared on an endoscopic table. The physician passes an endoscope, which has a diameter of approximately 12 mm, through the patient's mouth into the esophagus to view both the proximal and distal portions of the tumor to determine its morphology and character. If the endoscope will not cross through the tumor, the physician will dilate the lumen with a rigid dilator tracked over a guidewire or a balloon dilator which tracks through the endoscope. The endoscope is then passed retroflex so it looks back on itself and up at the most distal portion of the tumor to view its makeup. The physician measures the length of the tumor using graduated centimeter markings on the endoscope and/or makes a notation of the patient's incisor as to the most distal segment of the tumor. The physician then withdraws the endoscope partially and finds the most proximal segment of the tumor and makes a similar notation to determine the length of the tumor. Generally, the length of the stent is selected so that it extends about 2 cm beyond each end of the tumor.

Figure 2A:
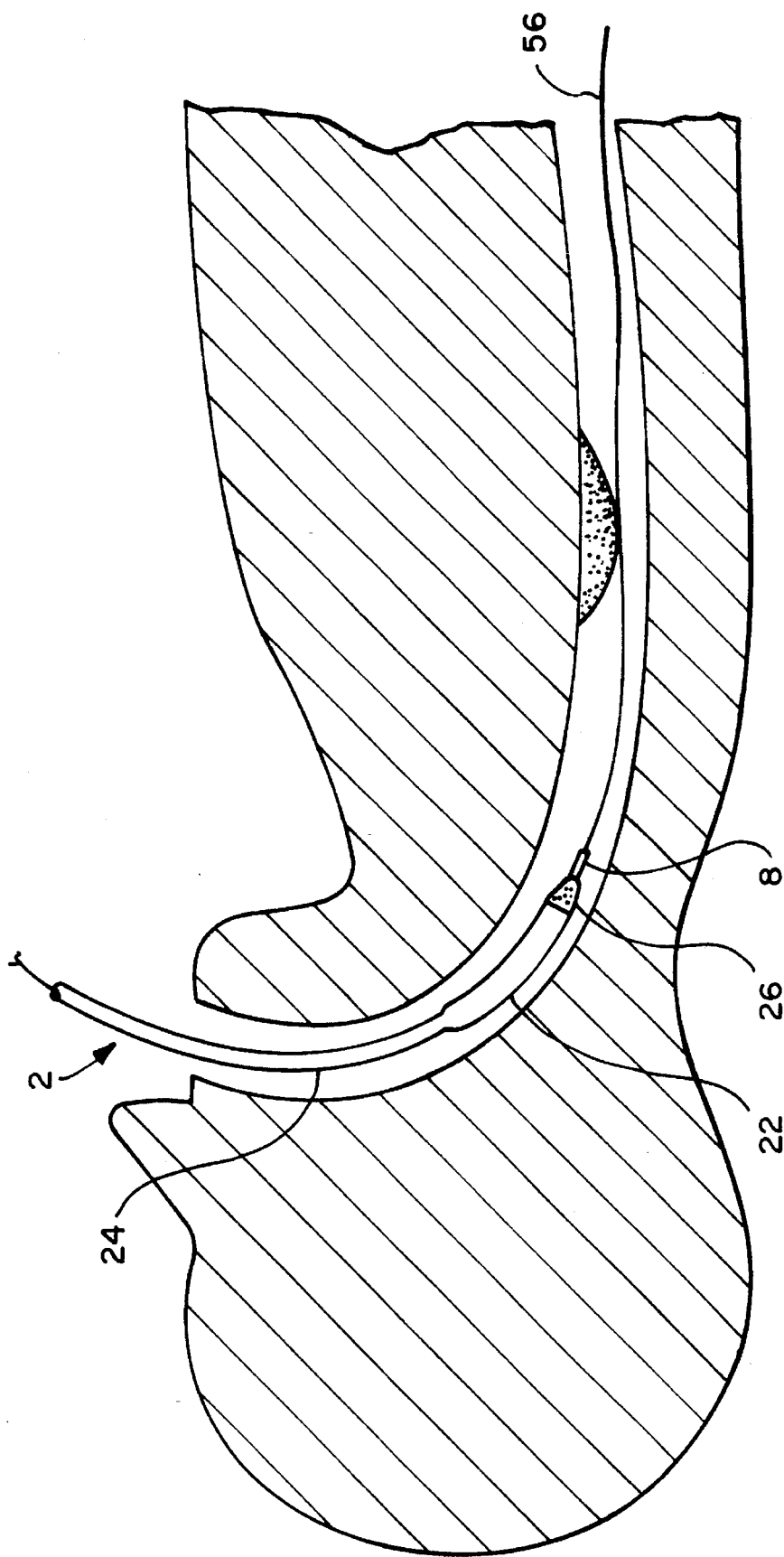
FIGS. 2–2h illustrate positioning a stent in the esophagus of a patient with a system according to the invention.
Figure 2B:
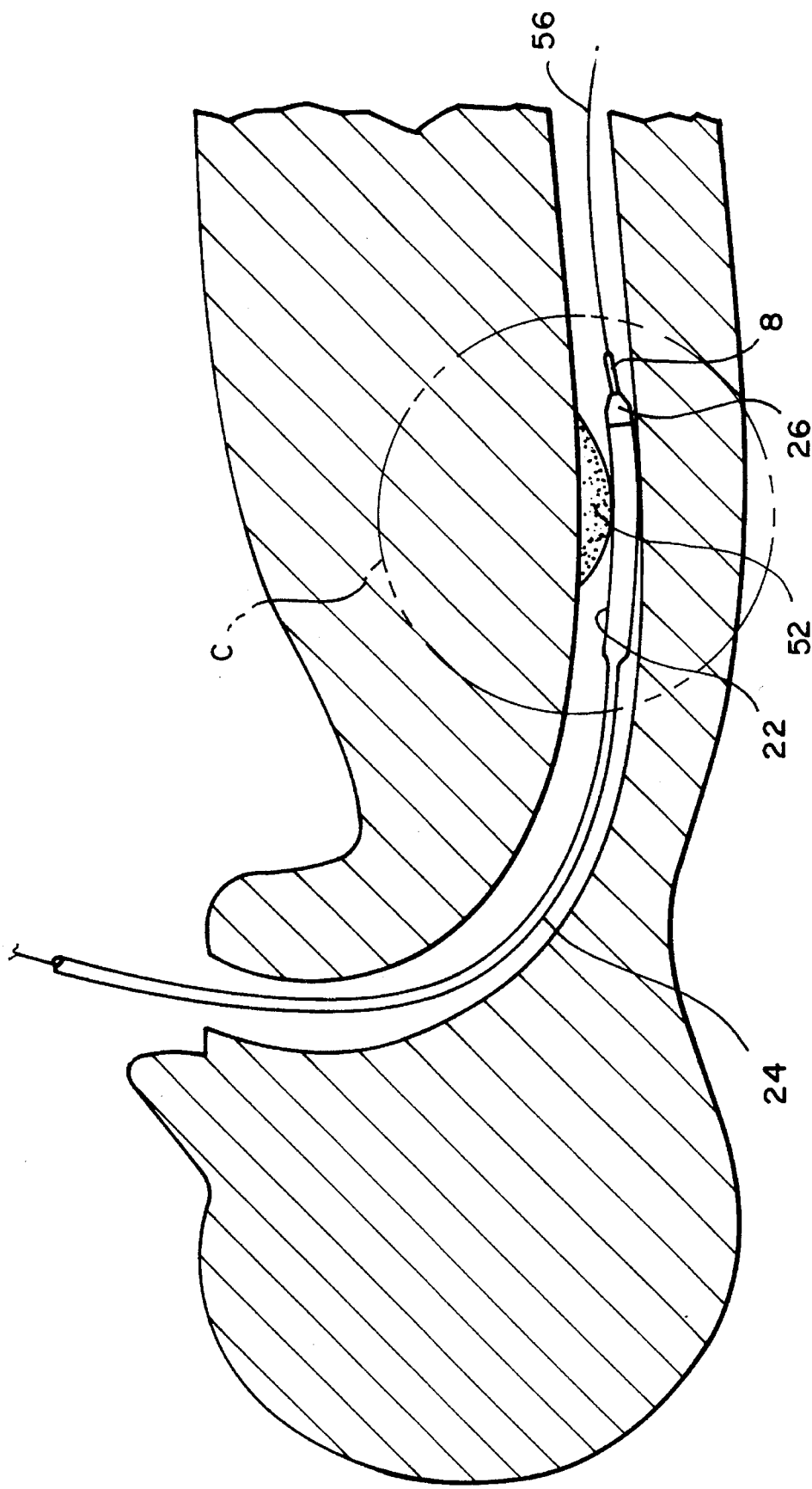
Figure 2C:
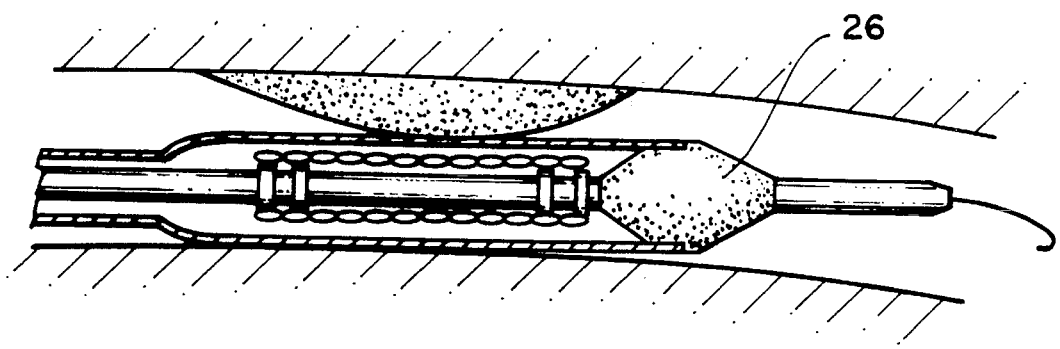
Figure 2D:
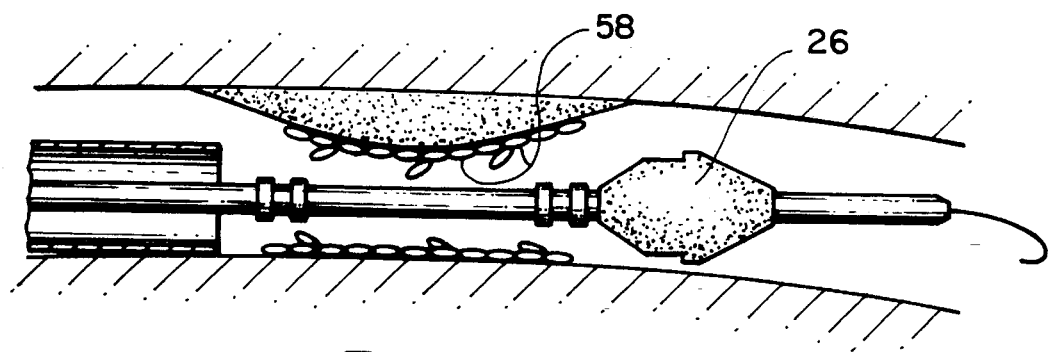
Figure 2E:
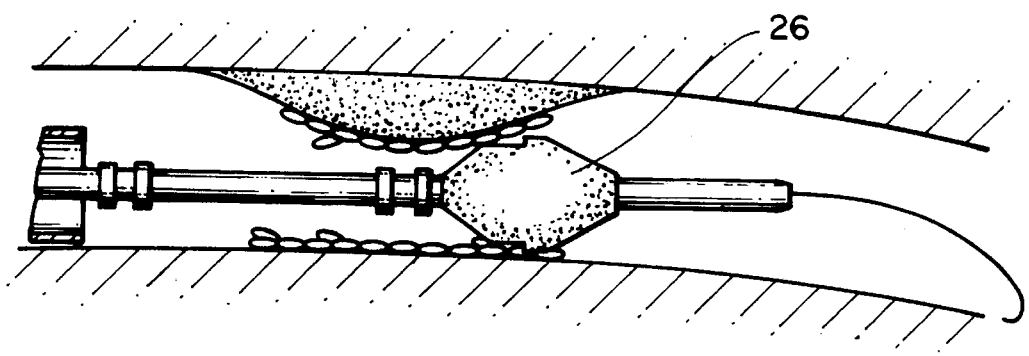
Figure 2F:
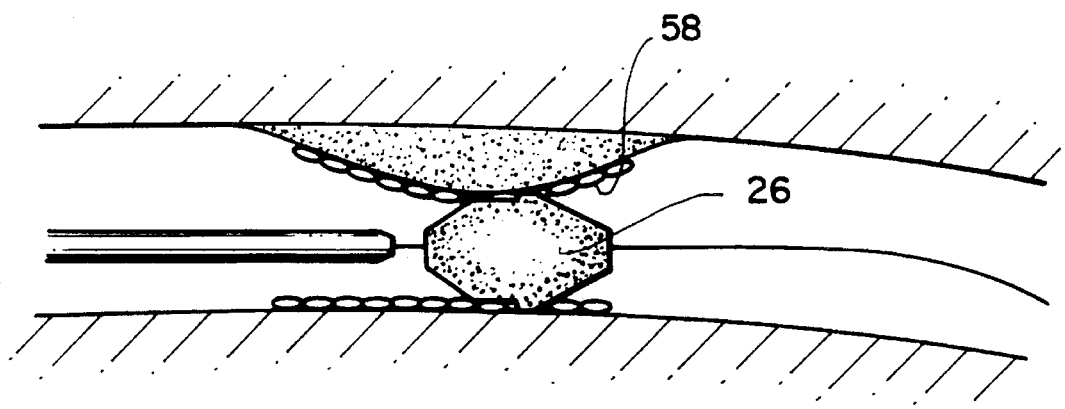
Figure 2G:
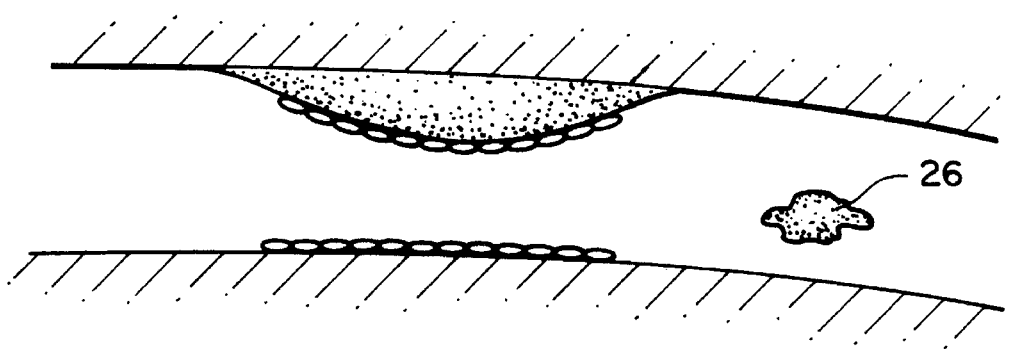
Figure 2H:
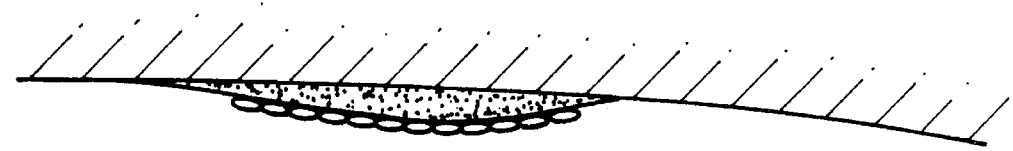
Figure 2H:
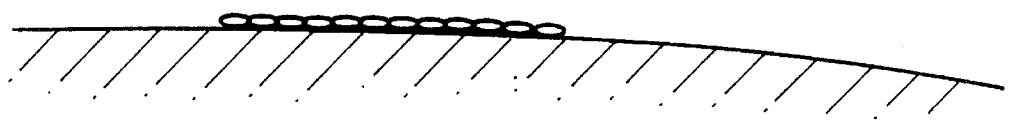

Referring to the series of FIGS. 2–2h, placement of a stent in the esophagus of a patient is illustrated. Referring to FIG. 2, the patient 50 having a tumor 52 in the esophagus 54, normally about 20 mm lumen diameter, but constricted to 8–12 mm by the tumor is treated by positioning a guidewire 56 through the throat into the esophagus to a position distal of the tumor 52, usually into the stomach.

Referring to FIG. 2a, the delivery system 2 is delivered over the guidewire by sliding the proximal portion of the guidewire through the guidewire lumen in the catheter. A lubricant, K-Y jelly, may be applied to the distal end 8 of the catheter. The physician then observes the placement with a fluoroscopic device using the radiopaque markers. As illustrated, the esophagus includes a highly torturous portion just distal of the throat including a 90 degree bend over a radius of about 6.35 cm. The distal end of the system, including the enlarged portion 22 of the sheath covering the stent, has sufficient strength to follow the contour of the wire without excessive kinking, which is enhanced by the support of the underlying stent. It should be appreciated that in this case, even if some kinking of the distal portion 22 of the sheath should occur as it passes the torturous bend, the kinks do not substantially impede the operation since the stent has not been located at a position at which the sheath would be withdrawn. As illustrated, the tip 26 provides a gradual increase in diameter, providing an atraumatic advance of the system into the esophagus.

Referring to FIGS. 2b and 2c (an enlarged view of the area in circle c) the distal portion of the system, corresponding to the position of the stent and the enlarged portion 22 of the sheath, is located across the constriction caused by the tumor 52. The atraumatic tip 26, with the gradual transition to larger diameter, aids in crossing the constricted region. In this position, the portions of the system including the reduced diameter portions 24 of the sheath are easily bent around the initial curve.

Referring to FIGS. 2d to 2h, enlarged views of the constricted region are shown to further illustrate the operation. Referring particularly to FIG. 2d, with the stent properly located about the constriction, the sheath is slid axially proximally to expose the stent to the body lumen. The gelatin holding the stent in compacted form is dissolved by body fluids and the stent self-expands to a larger diameter. As illustrated, in many instances, the stent initially expands the constriction to a small degree with a waist-shaped constriction still providing a rather narrow passageway with radial dimension somewhat smaller than the maximum radial dimension of the tip 26. The initial opening through the constriction may be formed, as mentioned, by a dilating means, so the opening is initially large enough to allow the system to cross with some clearance. However, the opening can be reduced somewhat after the system has crossed by a rebounding of the esophageal wall. In some cases, the system, with the atraumatic tip may be used to widen the constricted portion slightly so that the system can pass. Further, the stent, upon release from the catheter unwraps partially, leaving fold portions 58 that occlude the lumen partially. All of these conditions can create situations in which the tip is of a larger diameter than the constricted region of the lumen.

Referring to FIG. 2e, under these conditions, upon withdrawing the catheter, the tip 26 engages the stent in the region of the constriction. Referring to FIG. 2f, as withdrawal of the catheter continues, the catheter body slips through the inner lumen of the tip 26.

Referring to FIGS. 2g and 2h, after a short time, about 4 hours, the tip 26 dissolves and/or is passed through the body. In time, the radial force provided by the stent, further widens the esophagus providing a large open lumen that facilitates swallowing.

Other Embodiments

Figure 3:
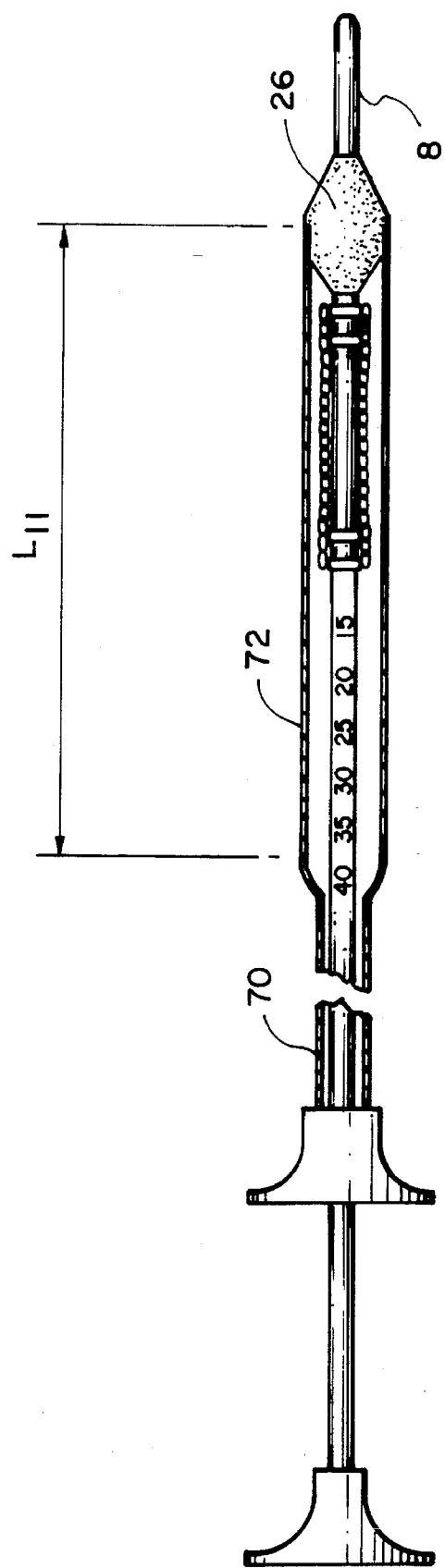
FIGS. 3–3b are cross-sectional side views of an alternative embodiment of the invention in several configurations.
Figure 3A:
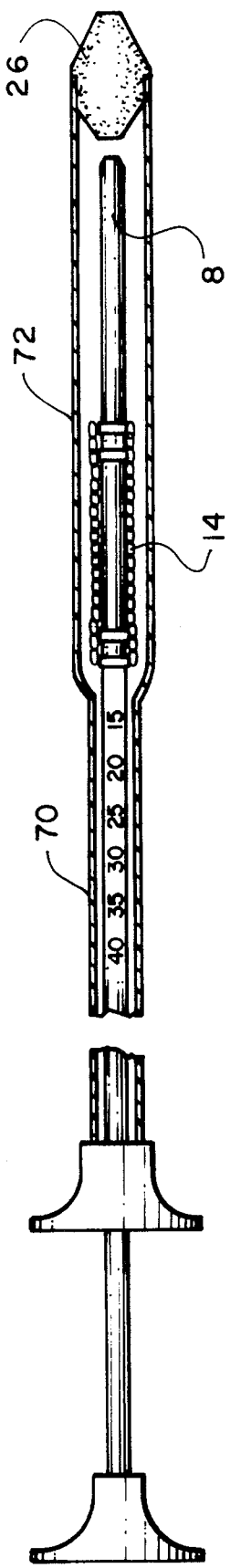
Figure 3B:
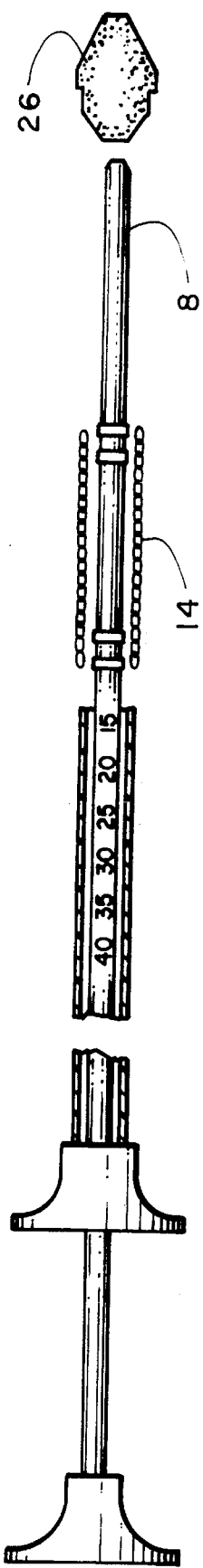

Many other embodiments are possible. For example, referring to FIG. 3, an embodiment is illustrated in which the tip 26 can be pushed off the end 8 of the catheter body by axial motion of a sheath 70 in the distal direction. In this case, the sheath has a distal portion 72 with a length, $L_{11}$, which is extended, compared to embodiments above, by at least the length of the distal end of the catheter. Referring to FIG. 3a, in this manner, when the sheath 70 is disposed axially distally, the distal end 72 can engage the tip 26 to push it off the end of the catheter 8 without disturbing the stent 14. Referring to FIG. 3b, after the atraumatic tip 26 has been pushed off the end 8 of the catheter body, the sheath can be retracted proximally to expose the stent 14 for expansion. With the tip 26 already having been removed from the end of the system, the catheter body and sheath can therefore be easily withdrawn and removed from the body. The construction according to this embodiment has the advantage that the axial force needed to push the tip 26 off the end of the catheter is not provided by engagement of the stent, which will therefore not be disturbed in removing the sheath and the catheter body from the patient.

Figure 4:
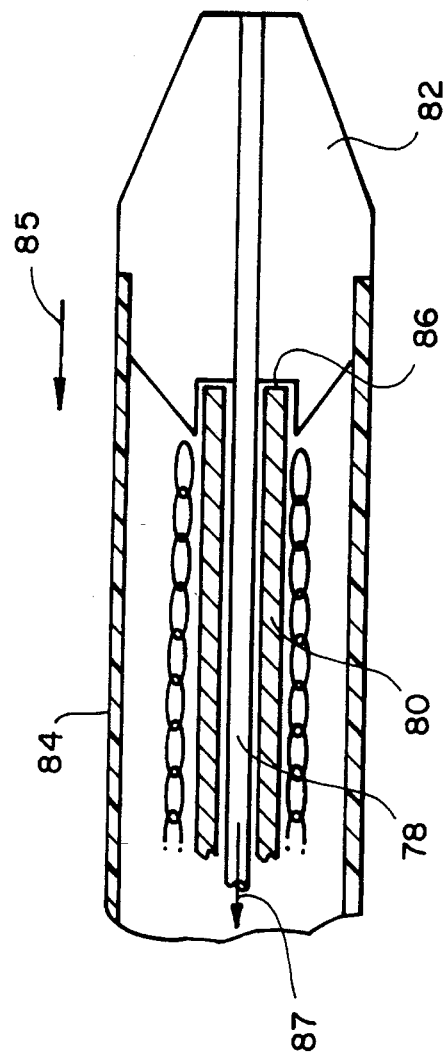
FIG. 4 is a cross-sectional view of yet another embodiment of the invention.

Referring to FIG. 4, in another embodiment, an actuator 78 is provided which runs coaxially within the catheter 80. The tip 82 has a clearance fit over the distal end of catheter 80 and is friction fit to the distal end of the actuator 78. The sheath 84 can be retracted (arrow 85) to expose the stent 14, as discussed above. The end 86 of the catheter inhibits axial proximal movement of the tip 82 during entry into the body and withdrawal of the sheath. The actuator 78 can be slid proximally (arrow 87) to slide the tip 82 off of its end and to leave it in the body.

The delivery systems can be sized and configured for use in various body lumens, the urethra or the biliary tree including the common bile duct, pancreatic duct and left and right hepatic ducts, and with particular benefit in alimentary tract lumens, such as the esophagus, stomach, pilorus, small intestine, colon or rectum. As will be appreciated, most of the latter applications involve relatively large lumens, about 1 to 1.5 cm or more, with torturous bends requiring relatively large stents to be delivered with large flexible delivery systems that resist kinking. As mentioned above, aspects of this invention provide particular advantages for delivering large stents, greater than about 10 mm expanded diameter, using larger delivery systems, greater than 6 mm maximum diameter. Like the esophagus, most of these lumens also have an extreme curvature near the entry point of the delivery system, such as the rectal sigmoid area in the colon. In the structure discussed in detail above, the stent is self-expanding and held compacted using a gelatin, but other embodiments uses a sheath that holds the stent in compacted form, without use of the gelatin. For example, the sheath may be constructed to hold the stent in compacted form by having a thicker wall in the distal portions and a thinner wall in proximal portions. The sheath may be formed in various ways, such as from polyethylene shrink tubing, which is reduced in diameter in proximal portions by heat application. In such cases, the wall thickness of the tubing is increased in the proximal portions, which can enhance the strength. The advantages of the invention can also be realized with stents that are not self-expanding, such as balloon expandable stents. A fluid, such as saline can be flowed into the lumen to more rapidly dissolve body-fluid dissolving portions.

Still further embodiments are within the following claims.

What is claimed is:

1. A system for delivering a prosthesis into the body of a patient, comprising:

a prosthesis, expandable from a radially compact form, an elongated catheter having a proximal end that remains outside the body, a distal end, and a supporting portion supporting said prosthesis in said radially compact form for delivery of the prosthesis to a desired location inside the body, and a dislodgeable atraumatic entry tip dislodgeably mounted on said catheter distal of said supporting portion, said tip having a diameter about equal to or greater than the prosthesis in said radially compact form, said atraumatic dislodgeable tip being selectively slidably dislodgeable off the catheter when said catheter is in the body in a manner that said catheter can be removed from the body leaving said tip inside the body.

2. The system of claim 1 wherein said prosthesis is self-expanding.

3. The system of claim 2 wherein said prosthesis is held in a radially compact form by a material which dissolves upon exposure to body fluids to thereby expand said prosthesis and said tip is formed of a material that dissolves upon exposure to body fluids.

4. The system of claim 3 further comprising a protective sheath over said prosthesis, that engages said tip to form a seal that protects said prosthesis from exposure to body fluids prior to removal of said sheath to expose said prosthesis.

5. The system of claim 3 wherein said tip is formed of a material that dissolves more slowly upon exposure to body fluids than said material that holds said prosthesis in radially compacted form dissolves upon exposure to body fluids.

6. The system of claim 1 wherein said tip is friction fit on said catheter.

7. The system of claim 6 wherein said prosthesis is expandable to diameters less than said diameter of said tip and axial force is provided by engaging said prosthesis and said tip by withdrawing said catheter proximally to slide said tip of the distal end of said catheter.

8. The system of claim 6 or 7 wherein the friction fit is overcome by an axial force of about 4 lbs. or less.

9. The system of claim 1 wherein said tip is formed of a substantially non-body fluid soluble polymer and is shaped and sized to pass the body.

10. The system of claim 6 wherein said tip has a generally cylindrical shape with a maximum diameter of about 8 mm.

11. The system of claim 1 wherein said tip is formed of a material which dissolves upon exposure to body fluids.

12. The system of claim 1 wherein said dislodgeable tip is mounted on said catheter proximal of said distal end, said tip tapering to the diameter of said distal end, and said distal end is highly flexible.

13. A system for delivering a prosthesis into the body of a patient, comprising:

a prosthesis, expandable from a radially compact form, an elongated catheter having a proximal end that remains outside the body, a distal end, and a supporting portion supporting said prosthesis in said radially compact form for delivery of the prosthesis to a desired location inside the body;

a dislodgeable atraumatic entry tip dislodgeably mounted on said catheter distal of said supporting portion, said tip having a diameter about equal to or greater than the prosthesis in the radially compact form, said atraumatic dislodgeable tip being selectively slidably dislodgeable off the catheter when said catheter is in the body in a manner that said catheter can be removed from the body leaving the tip inside the body, and a protective sheath having a distal portion with an inner diameter sized to be coaxially disposed about said prosthesis during delivery into the body, said sheath being constructed to engage said tip and to be axially slidable to slide said tip off the distal end of said catheter.

14. The system of claim 13 wherein said distal portion of said sheath has a length greater than the length of said prosthesis.

15. A system for delivering a prosthesis into the body of a patient, comprising:

a prosthesis, expandable from a radially compact form, an elongated catheter having a proximal end that remains outside the body, a distal end, and a supporting portion supporting said prosthesis in said radially compact form for delivery of the prosthesis to a desired location inside the body, and a dislodgeable atraumatic entry tip dislodgeably mounted on said catheter distal of said supporting portion, said tip having a diameter about equal to or greater than the prosthesis in the radially compact form, and an actuator extending coaxially with said catheter wherein said tip is friction fit on said actuator at a location distal of said catheter such that said tip can be slidably dislodged off said catheter by relative axial movement of said catheter and said actuator to slide said tip off said actuator by engaging said tip with said catheter said tip being slidably dislodged in a manner that the catheter can be removed from the body leaving the tip inside the body.

16. A method for delivering a prosthesis into the body of a patient, comprising:

providing a prosthesis expandable from a radial compact form and an elongated catheter having a proximal end that remains outside the body, a distal end, and a supporting portion supporting said prosthesis in said radially compact form, said catheter further including a dislodgeable atraumatic tip dislodgeably mounted on the catheter distal of said supporting portion and having a diameter about equal to or greater than the prosthesis in said radial compact form, placing said catheter into a body lumen and positioning said prosthesis at a desired location, expanding said prosthesis to a diameter such that the tip cannot pass through the prosthesis, removing said tip from said catheter in a manner that said catheter can be removed from the body leaving said tip inside the body, and withdrawing said catheter through said expanded prosthesis.

17. The method of claim 16 wherein removing said tip comprises withdrawing said catheter so that said tip engages said prosthesis, and continuing to withdraw said catheter so said tip slides axially off the end of said prosthesis.

18. The method of claim 16 or 17 comprising, selecting a self-expanding prosthesis to provide axial force to the interior of said lumen to fully expand said lumen after an extended period of time, and withdrawing said catheter prior to fully expanding said prosthesis.

19. The method of claim 16 comprising placing said catheter in the esophagus.

20. The method of claim 16 comprising placing said catheter in the biliary.

21. The method of any one of claims 16, 17, 18, or 20 wherein said prosthesis is self-expanding.

* * * * *